United States Patent [19]

Falling et al.

[11] Patent Number: 5,238,889

[45] Date of Patent: Aug. 24, 1993

[54] PROCESS FOR THE SEPARATION OF OLIGOMERIC MATERIALS FROM A CATALYST MIXTURE

[75] Inventors: Stephen N. Falling, Kingsport, Tenn.; Stephen A. Godleski, Fairport; Lynda W. McGarry, North Chili, both of N.Y.

[73] Assignee: Eastman Kodak Company, Rochester, N.Y.

[21] Appl. No.: 926,421

[22] Filed: Aug. 10, 1992

[51] Int. Cl.$^5$ .................. B01J 31/40; B01J 38/68; B01J 38/48; C07D 307/28

[52] U.S. Cl. .................. 502/24; 502/22; 502/31; 502/32; 502/155; 502/164; 549/507; 549/539

[58] Field of Search ............. 502/24, 22, 31, 32; 549/507, 539

[56] References Cited

U.S. PATENT DOCUMENTS 2,680,109  6/1954  Stevens et al. .................. 502/539
4,946,817  8/1990  Bertram et al. .................. 502/155
5,082,956  1/1992  Monnier et al. .................. 549/507

Primary Examiner—Paul E. Konopka
Attorney, Agent, or Firm—J. Frederick Thomsen; William P. Heath, Jr.

[57] ABSTRACT

Disclosed is a process for the recovery of catalyst values from mixtures of catalyst compounds and oligomeric materials. The process provides for the separation of (i) an onium iodide compound, (ii) an organotin iodide compound, or (iii) a mixture thereof from a mixture thereof in an oligomer of a $\gamma,\delta$-epoxy-alkene by the steps of (1) intimately contacting the mixture with an extraction solvent selected from hydrocarbons having about 5 to 12 carbon atoms; (2) allowing the mixture of step (1) to separate into 2 phases; and (3) recovering the extraction solvent phase containing iodide compounds (i) and (ii). The oligomer mixture of compounds (i) and/or (ii) is formed during the manufacture of 2,5-dihydrofurans by the isomerization of $\gamma,\delta$-epoxyalkenes.

7 Claims, No Drawings

PROCESS FOR THE SEPARATION OF OLIGOMERIC MATERIALS FROM A CATALYST MIXTURE

This invention pertains to a process for the recovery of catalyst values from mixtures of catalyst and oligomeric materials. More specifically, this invention pertains to a process for the recovery of the components of a catalyst system utilized in the manufacture of 2,5-dihydrofurans by the isomerization of $\gamma,\delta$-epoxyalkenes.

The preparation of $\gamma,\delta$-epoxyalkenes by the selective monoepoxidation of butadiene and analogous dienes is described in U.S. Pat. Nos. 4,897,498 and 4,950,773. U.S. Pat. No. 5,082,956 discloses processes for the preparation of 2,5-dihydrofurans by isomerizing $\gamma,\delta$-epoxyalkenes in the presence of catalyst systems comprising certain onium iodide compounds and, optionally, an inorganic Lewis acid and/or certain organometallic halide compounds. The disclosed processes include vapor phase processes wherein a vapor of the $\gamma,\delta$-epoxyalkene reactant is passed through a reaction zone containing the catalyst system which is in the form of a molten salt or a film deposited on a non-acidic support material. This gas phase process employs an inert gas diluent such as nitrogen or helium and is conducted at a temperature above the melting point of the catalytically-active catalyst components, typically at a temperature of 130° to 150° C.

In another embodiment of the isomerization process disclosed in U.S. Pat. No. 5,082,956, $\gamma,\delta$-epoxyalkenes are isomerized to dihydrofurans in the liquid phase using a solution of the above-described catalyst system in an extraneous, inert solvent and a temperature of 100° to 150° C. This procedure uses a hydrocarbon or halogenated hydrocarbon solvent, such as mesitylene, pseudocumene or dichlorobenzene, having a boiling point higher than the 2,5-dihydrofuran product to facilitate isolation of the product from the catalyst solution by distillation. 2,5-Dihydrofuran may be hydrogenated as described in U.S. Pat. No. 4,962,210 to tetrahydrofuran, a valuable compound useful as a chemical process solvent and as an intermediate in the preparation of polymers such as poly(tetramethylene ether) glycol.

A particularly convenient means for the preparation of dihydrofurans by the isomerzation of $\gamma,\delta$-epoxyalkenes comprises a liquid phase, continuous process wherein a $\gamma,\delta$-epoxyalkene initially is fed to a melt of the catalyst system and thereafter is continuously fed to a solution of the catalyst in the 2,5-dihydrofuran product. The 2,5-dihydrofuran product may be recovered from the mixture by conventional distillation procedures. A catalyst system which has been found to be especially effective comprises an onium iodide compound such as an ammonium or phosphonium iodide and an organotin compound such as a trihydrocarbyltin iodide.

Unavoidable side products of the isomerization of $\gamma,\delta$-epoxyalkenes to dihydrofurans are $\alpha,\beta$-unsaturated carbonyl compounds such as crotonaldehyde (about 0.5 3%) and an oligomer of the $\gamma,\delta$-epoxyalkene (about 1-6%). The $\alpha,\beta$-unsaturated carbonyl compound by product is removed from the reaction mixture as a vapor during product recovery. However, the, oligomer is non volatile and accumulates in the catalyst solution, increasing the volume and viscosity of the catalyst solution and decreasing catalyst concentration,. It is apparent that operation of a continuous, commercial-scale process for isomerizing $\gamma,\delta$-epoxyalkenes to dihydrofurans is not feasible unless a means is provided for removing some or all of the oligomer from the isomerization process. For the isomerization process to be economically feasible and environmentally acceptable, the recovery and reuse of the expensive catalyst components is imperative.

We have discovered an efficient process for the separation of the catalyst components from the above-described oligomer which permits batch, semi-continuous or continuous operation of the isomerization reaction. The catalyst/oligomer separation is accomplished in accordance with the present invention by a liquid-liquid extraction process in which the catalyst compounds are preferentially extracted from the catalyst/oligomer mixture. The catalyst/extractant phase is separated from the oligomer phase and the solvent removed to give a catalyst mixture which may be reused in the isomerization reaction.

The present invention therefore provides a process for the separation of a catalyst system comprising (i) an onium iodide compound, (ii) an organotin iodide compound, or (iii) a mixture thereof from a mixture of the catalyst system and an oligomer of a $\gamma,\delta$-epoxyalkene by the steps comprising:

(1) intimately contacting the mixture with an extraction solvent selected from hydrocarbons having about 5 to 12 carbon atoms and chlorocarbons;

(2) allowing the mixture of step (1) to phase separate; and (3) recovering the extraction solvent phase containing iodide compounds (i) and/or (ii).

As explained hereinabove, the oligomer referred to in the above process description is formed as a non-volatile, by-product of an isomerization process wherein the $\gamma,\delta$-epoxyalkene is isomerized to the corresponding 2,5-dihydrofuran. The isomerization process typically is carried out by heating, e.g., at temperatures in the range of about 65° to 160° C., the $\gamma,\delta$-epoxyalkene in the liquid phase in the presence of a catalyst system comprising (i) an onium iodide compound, (ii) an organotin iodide compound or (iii) a mixture thereof. The oligomer is a low molecular weight polyether formed as the result of ring-opening polymerization of the $\gamma,\delta$-epoxyalkene reactant in a manner analogous to the formation of polyether oligomers and polymers from ethylene oxide and propylene oxide.

The extraction solvent (extractant) employed may be selected from a variety of hydrocarbons and chlorocarbons depending, for example, upon the particular $\gamma,\delta$-epoxybutene reactant and catalyst components used in the isomerization process. Generally, the extractant should satisfy four requirements: (1) it should form a separate liquid phase at equilibrium when contacted with a mixture of the catalyst components and the oligomer, (2) it should have a higher selectivity for dissolving the catalyst components than the oligomer, (3) it should have characteristics that enable it to be separated from the catalyst components by evaporation, distillation, crystallization, or some other separation operation, and (4) it should be inert to the catalyst components, starting material and products. It is possible that an extraction solvent may function both as the solvent for the isomerization reaction and the oligomer removal process if the dihydrofuran product is removed prior to phase separation. In general, the extraction solvent should be non-polar to avoid dissolving the oligomer. The extraction solvent may comprise a mixture of two or more solvents.

Examples of extraction solvents include cyclic and straight- and branched-chain, acyclic alkanes containing from about 5 to 12 carbon atoms. Specific examples of the acyclic alkane extractants include pentane, hexane, heptane, octane, nonane, decane, mixed hexanes, mixed heptanes, mixed octanes, isooctane, Stoddard solvent, and the like. Examples of the cycloalkane extractants include cyclopentane, cyclohexane, cycloheptane, cyclooctane, methylcyclohexane, etc. Alkenes such as hexenes, heptenes, octenes, nonenes and decenes; aromatic hydrocarbons such as benzene, toluene, xylene, mesitylene; and chlorocarbons such as carbon tetrachloride also may be used as the extractant. The preferred extraction solvents are alkanes having about 6 to 12 carbon atoms. When the $\gamma,\delta$-epoxyalkene reactant is 3,4-epoxy-1-butene, the extractant preferably is a straight-chain alkane of about 6 to 2 carbon atoms, especially heptane, octane, nonane, and decane.

The onium iodide compound involved in the present invention may be selected from a variety of tetra (hydrocarbyl) ammonium iodides and tetra (hydrocarbyl) phosphonium iodides, preferably having a total carbon atom content of about 16 to 72 carbon atoms. Such compounds have the formulas

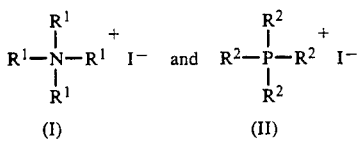

wherein each $R^1$ substituent independently is selected from alkyl of up to about 20 carbon atoms and each $R^2$ substituent is independently selected from $R^1$, benzyl, phenyl or phenyl substituted with up to 3 substituents selected from lower alkyl, e.g., alkyl of up to about 4 carbon atoms, lower alkoxy or halogen; or two $R^1$ substituents collectively may represent alkylene of 4 to 6 carbon atoms including alkylene of 4 to 6 carbon atoms substituted with lower alkyl; provided, as specified above, that the quaternary iodide compounds contain about 16 to 72 carbon atoms. Specific examples of the onium iodide catalyst component which may be recovered according to the present invention include tetra-n-octylphosphonium iodide, tri-n-octyl(n-dodecyl)phosphonium iodide, tri-n-octyl(n-hexadecyl)-phosphonium iodide, tri-n-octyl(n-octadecyl)phosphonium iodide, tetra-n-dodecylphosphonium iodide, tetra-n-hexadecylphosphonium iodide, tetra-n-octadecylphosphonium iodide, tetra-n-dodecylammonium iodide, tetra-n-hexadecylammonium iodide, and tetra-n-octadecylammonium iodide. The preferred onium iodides are tetra-n-alkylphosphonium iodides containing about 32 to 72 carbon atoms, especially compounds of formula (II) above wherein each $R^2$ is straight chain alkyl of about 4 to 18 carbon atoms. Tetra-n-dodecylphosphonium iodide, tetra-n-hexadecylphosphonium iodide, and tri-n-octyl(n-octadecyl)phosphonium iodide are especially preferred.

The organotin catalyst component may be selected from organotin (IV) iodides such as hydrocarbyltin triiodides, di(hydrocarbyl)tin diiodides, and tri(hydrocarbyl) tin iodides. Examples of such organotin (IV) iodide compounds have the general formula $$(R^3)_n-Sn-I_{(4-n)} \quad (III)$$

wherein each $R^3$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms; and n is 1, 2, or 3.

Specific examples of the organotin compounds include di-n-butyltin diiodide, tri-n-butyltin iodide, tri-n-octyltin iodide, triphenyltin iodide, trimethyltin iodide, n-butyltin triiodide, tricyclohexyltin iodide, tris-(2-methyl-2-phenylpropyl)tin iodide, tribenzyltin iodide, dimethyltin diiodide and diphenyltin diiodide. Other organotin halides such as chlorides and bromides may be used in the process wherein they are converted to the iodide compounds. The preferred organotin iodide compounds have the general formula:

$$(R^3)_3-Sn-I \quad (IV)$$

wherein each $R^3$ independently is selected from alkyl having about 4 to 10 carbon atoms or phenyl. Tri-n-octyltin iodide and triphenyltin iodide are especially preferred.

The ratio of the onium iodide and organotin iodide components of the catalyst system can vary substantially depending, for example, upon the particular compounds used. Generally, the quaternary onium iodide:organotin iodide mole ratio is within the range of about 20:1 to 0.05:1. For the preferred catalyst system comprising a phosphonium iodide and an organotin iodide, a phosphonium iodide:organotin iodide mole ratio of about 5:1 to 0.2:1 is especially preferred.

The catalyst recovery process of this invention may be carried out in a batch, semi-continuous or continuous mode of operation. For example, batch operation may comprise removal of the volatile components from the isomerization reaction mixture by distillation followed by addition of the extraction solvent, agitation, settling, and phase separation. We prefer to remove all, or substantially all, of the volatile components from the catalyst/oligomer mixture since the volatiles, i.e., the 2,5-dihydrofuran, the $\gamma,\delta$-epoxyalkene reactant and the $\alpha,\beta$-unsaturated carbonyl compound, solubilize some of the oligomer in the extraction solvent. The volatile components of the catalyst system typically constitute 5 to 30 weight percent of the catalyst/oligomer mixture that is extracted. One of the layers or phases comprises the extraction solvent containing the onium iodide and organotin iodide catalyst components. The second oligomer layer may be extracted repeatedly as needed to give the desired degree of catalyst recovery. The combined solvent layers are concentrated by solvent evaporation or distillation to give a crude catalyst mixture which usually is handled as a molten liquid and is recycled to the isomerization process reactor without further purification. A fraction of the original oligomer content is usually still present in this crude catalyst mixture. The oligomer layer may be used as a by-product or sent for disposal. It may be possible to recover one or both of the catalyst components by the crystallization thereof from the extraction solvent.

The temperature of the extraction/separation process normally is controlled at a slightly elevated temperature to ensure good solubility of catalysts in the solvent and decreased oligomer viscosity. The temperature preferably is held below the boiling point of the solvent so that the process may be operated at atmospheric pressure. The process normally is carried out at a temperature of about 40° to 125° C.

Our novel extraction process preferably is operated continuously or semi continuously in a countercurrent manner. This technique, as is well known in the art, can give excellent efficiencies of extraction. See, for example, T. C. Lo, M. H. I. Baird, C. Hanson, Handbook of Solvent Extraction, Reprint Edition, Krieger Publishing Company, Malabar, Fla., 1991. Typical countercurrent extraction systems include the mixer/settler, baffle-tray column, Kuhni column, rotating disk contactor, and Karr reciprocating plate column. In the continuous mode of operation, a portion of the catalyst/oligomer mixture is removed from the reactor and volatile materials are evaporated off. The concentrated mixture is then fed to the continuous multistage extractor in a direction countercurrent to the flow of the extraction solvent. As in the batch operation, the catalyst solution is concentrated to give the non-volatile catalyst components and recovered solvent. As mentioned above, it may be possible to isolate the catalyst components from the catalyst solution by crystallization.

The concentration of the onium iodide and organotin iodide compounds in the oligomer material which is extracted in accordance with our invention typically is in the range of about 20 to 90 weight percent based on the total weight of the catalyst/oligomer mixture. The amount of extraction solvent employed can vary substantially depending, for example, on the particular onium iodide and organotin iodide compounds present in the oligomer material, the extraction solvent being used, and the manner in which the extraction process is operated. However, the weight ratio of the extraction solvent to the catalyst/oligomer mixture to be extracted normally is in the range of about 10:1 to 0.1:1.

The γ,δ-epoxyalkene reactants may contain from 4 to about 8 carbon atoms. Examples of the epoxyalkene and epoxycycloalkene reactants include compounds having the structural formula:

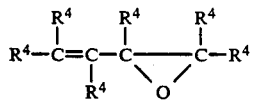
(V)

wherein each $R^4$ is independently selected from hydrogen and methyl or 2 $R^4$ substituents collectively may represent an alkylene radical which forms a ring having about 5 to 8 carbon atoms. The preferred epoxyalkene reactants comprise compounds of formula (V) wherein a maximum of four of the $R^4$ substituents individually may represent methyl. Exemplary compounds contemplated for use in the practice of the present invention include 3,4-epoxy 3-methyl-1-butene, 3,4-epoxy-2-methyl-1-butene, 2,3-dimethyl-3,4-epoxy-1-butene, 3,4-epoxy-1-butene, 2,5-dimethyl-2,4-hexadiene monoepoxide 3,4-epoxycyclooctene and the like. The epoxyalkene reactant of primary interest is 3,4-epoxy-1-butene. The 2,5-dihydrofuran compounds obtained in accordance with our novel process have the structural formula:

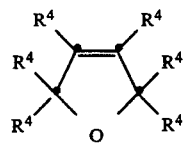
(VI)

wherein the $R^4$ substituents are defined above. Of the compounds which may be obtained in accordance with our invention, the most important is 2,5-dihydrofuran.

A particularly preferred embodiment of our invention is represented by the process for the separation of a catalyst system comprising (i) an onium iodide compound and (ii) an organotin iodide compound, from a mixture of the catalyst system and an oligomer of a 3,4-epoxy-1-butene by the steps comprising:

(1) intimately contacting the mixture with an extraction solvent selected from alkanes having about 6 to 2 carbon atoms;

(2) allowing the mixture of step (1) to phase separate; and (3) recovering the extraction solvent phase containing iodide compounds (i) and (ii);

wherein the onium iodide compound is a phosphonium iodide containing about 32 to 72 carbon atoms and having the general formula

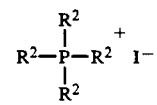

wherein each $R^2$ substituent is independently selected from straight-chain alkyl of about 4 to 8 carbon atoms; and the organotin iodide compound has the formula $(R^3)_3$—Sn—I wherein each $R^3$ independently is selected from alkyl having about 4 to 10 carbon atoms or phenyl.

The process of the present invention is further illustrated by the following examples wherein distillates were analyzed by gas chromatography on a Hewlett Packard 5890A gas chromatograph with a DB5-30W capillary column; temperature program 35° C. (4.5 minutes), 20° C./minute to 260° C. (hold 6 minutes).

Catalyst and oligomer samples were analyzed by $^1$H NMR on a Varian Gemini 300 spectrometer (300 MHz) using deuterochloroform as solvent and, tetramethylsilane as internal standard. Analyses are reported in weight percent. In the examples, "conversion" and "selectivity" are based on the composition of the distillates and refer, respectively, to:

$$\text{Selectivity} = \frac{\text{Weight Percent DHF}}{\text{Weight Percent DHF + Weight Percent HCr}}$$

in which EpB refers to 3,4-epoxy-1-butene, DHF refers to 2,5-dihydrofuran and HCr refers to crotonaldehyde. The amounts of materials fed and materials recovered in the examples may not balance due to, losses resulting from evaporation, material transfers, leaks, etc.

EXAMPLE 1

Isomerization

Triphenyltin iodide (25.0 g), tri-n-octyl(n-octadecyl) phosphonium iodide (39.4 g), and 2,5-dihydrofuran (10.0 g) were placed in a 200-mL, four neck, round-bottom flask equipped with a thermocouple, magnetic stirrer, distillation head, oil heating bath and reactant feed tube. The mixture was heated to 105 ° C. and feeding of 3,4-epoxy-1-butene addition was begun while maintaining the temperature at approximately 105° C. A total of 2431 g of 3,4-epoxy-1-butene was added over a period of 40 hours. The pressure within the flask was gradually lowered to about 100 torr to completely distill the volatile components from the catalyst/oligomer residue. A total of 2369 g of distillate was collected (97.4% weight recovery). The composition of the distillate was 6.50% 3,4-epoxy-1-butene, 92.5% 2,5-dihydrofuran, and 0.95% crotonaldehyde. The conversion of 3,4-epoxy-1-butene was 93.5% and selectivity to 2,5-dihydrofuran was 99.0%.

Extraction

The extractions in this and subsequent examples were carried out in a 500-mL, jacketed, glass vessel equipped with a mechanical stirrer, thermocouple, and bottom stopcock. Each extraction mixture was heated to a constant temperature (±1° C.) by circulating heated glycol/water from a constant temperature bath to the jacket. The catalyst/oligomer mixture was added to the alkane extraction solvent and heated to the desired temperature while stirring vigorously. The extraction mixture was stirred for at least 5 minutes, stirring was discontinued and the layers were allowed to completely separate.

In this example, heptane (150 mL) was added to the stripped catalyst/oligomer residue (approximately 90 g) and the mixture was agitated while being heated to 65°–75° C. and then allowed to separate into two layers. The layers were separated and the bottom (oligomer) layer was extracted as described above two more times with 150 mL portions of heptane. The heptane layers were combined and the solvent removed by rotary vacuum evaporation (to about 70° C. and 30 torr). The catalyst-containing material (80.3 g) thus recovered had the following approximate composition: 32.9% triphenyltin iodide, 51.8% tri-n-octyl(n-octadecyl)phosphonium iodide, and 15.3% oligomer. The amount of oligomer removed by the extraction procedure was 8.7 g.

EXAMPLE 2

Isomerization

The catalyst-containing material recovered in Example 1 was returned to the reaction flask and the isomerization procedure was repeated. Over a period of 28 hours, a total of 1728 g of 3,4-epoxy-1-butene was added and 1648 g of distillate was collected (95.4% weight recovery). The conversion of 3,4-epoxy-1-butene was 92.1% and selectivity to 2,5-dihydrofuran was 97.8%.

Extraction

The catalyst/oligomer residue remaining from the isomerization process was extracted by the procedure described in Example 1. The catalyst-containing material thus recovered had the following approximate composition: 17.1% triphenyltin iodide, 44.6% tri-n-octyl(n-octadecyl)phosphonium iodide, and 38.3% oligomer. The amount of oligomer removed by the extraction procedure was 30.7 g.

EXAMPLE 3

Isomerization

The catalyst-containing material recovered in Example 2 was returned to the reaction flask and the isomerization procedure was repeated. Over a period of 12 hours, a total of 669 g of 3,4-epoxy-1-butene was added and 623 g of distillate was collected (93.1% weight recovery). The conversion of 3,4-epoxy-1-butene was 88.9% and selectivity to 2,5-dihydrofuran was 98.9%.

Extraction

The catalyst/oligomer residue remaining from the isomerization process was extracted by the procedure described in Example 1. The catalyst-containing material (112.5 g) thus recovered had the following approximate composition: 19.0% triphenyltin iodide, 47.2% tri-n-octyl (n-octadecyl) phosphonium iodide, and 33.7% oligomer. The amount of oligomer removed by the extraction procedure was 33.6 g.

EXAMPLE 4

Isomerization

The catalyst-containing material recovered in Example 3 was returned to the reaction flask and the isomerization procedure was repeated. Over a period of 21 hours, a total of 977 g of 3,4-epoxy-1-butene was added and 916 g of distillate was collected (93.8% weight recovery). The conversion of 3,4-epoxy-1-butene was 76.4% and selectivity to 2,5-dihydrofuran was 98.9%.

Determination of Distribution Coefficients and Extraction Selectivities

The extraction apparatus described in Example 1 was used in the determination of the distribution coefficients for triphenyltin iodide, tri-n-octyl-(n-octadecyl) phosphonium iodide, and oligomer. The catalyst/oligomer residue remaining from the above isomerization process was vigorously mixed with either octane or heptane at a temperature of 40°, 60° or 80° C. The extraction mixture was allowed to separate into two layers and a small sample of each layer was taken by syringe, weighed, rotary evaporated to about 70° C. and 30 torr, reweighed to determine weight loss (the amount of alkane removed), and analyzed by NMR to determine the amount of triphenyltin iodide, tri-n-octyl(n octadecyl)-phosphonium iodide, and oligomer present. Then additional alkane was added to the mixture and the extraction, sampling and analysis were repeated as described above. Three or four dilutions were performed for each solvent-temperature combination to calculate distribution coefficients and extraction selectivities.

Using the values thus obtained, the distribution coefficients for triphenyltin iodide, tri-n-octyl(n-octadecyl)-phosphonium iodide, and oligomer were calculated:

$$\text{Distribution Coefficient} = M_x = \frac{\text{Weight percent } X \text{ in alkane layer}}{\text{Weight percent } X \text{ in oligomer layer}}$$

The extraction selectivities for the triphenyltin iodide and tri-n-octyl(n-octadecyl)phosphonium iodide are calculated by dividing their distribution coefficients by the related oligomer distribution coefficient.

The catalyst/oligomer residue remaining from the isomerization process of Example 4 was extracted according to the procedure described using the following alkane-temperature combinations:

Example 4A—Octane, 40° C.
Example 4B—Octane, 60° C.
Example 4C—Heptane, 60° C.
Example 4D—Heptane, 80° C.

The average of the distribution coefficients and the extraction selectivities determined are shown in Table I wherein SNI, PHOS and OLIG refer to the organotin iodide compound, the phosphonium iodide compound and the oligomer present in each example.

EXAMPLE 5

Isomerization

The procedure of Example 1 was repeated except that the initial charge of materials was triphenyltin iodide (25.0 g), tetra-n-dodecylphosphonium iodide (44.0 g), and 2,5-dihydrofuran (10.0 g). Over a period of 17 hours, a total of 1061 g of 3,4-epoxy-1-butene was added and 1041 g of distillate was collected (99.0% weight recovery). The conversion of 3,4-epoxy-1-butene was 93.6% and selectivity to 2,5-dihydrofuran was 99.0%.

Extraction

The catalyst/oligomer residue remaining from the isomerization process was extracted with octane using the procedure described in Example 1. The catalyst-containing material (76.8 g) thus recovered had the following approximate composition: 31.2% triphenyltin iodide, 62.3% tetra-n-dodecylphosphonium iodide, and 6.5% oligomer.

EXAMPLE 6

Isomerization

The catalyst-containing material recovered in Example 5 was returned to the reaction flask and the isomerization procedure was repeated. Over a period of 21 hours, a total of 1311 g of 3,4-epoxy-1-butene was added and 1267 g of distillate was collected (96.6% weight recovery). The conversion of 3,4-epoxy-1-butene was 91.1% and selectivity to 2,5-dihydrofuran was 99.4%.

Extraction

The catalyst/oligomer residue remaining from the isomerization process was extracted with octane by the procedure described in Example 1. The catalyst-containing material (92.2 g) thus recovered had the following approximate composition: 23.8% triphenyltin iodide, 53.1% tetra-n-dodecylphosphonium iodide, and 23.1% oligomer. The amount of oligomer removed by the extraction procedure was 18.3 g.

EXAMPLE 7

Isomerization

The catalyst-containing material recovered in Example 6 was returned to the reaction flask and the isomerization procedure was repeated. Over a period of 18 hours, a total of 795 g of 3,4-epoxy-1-butene was added and 730 g of distillate was collected (91.8% weight recovery). The conversion of 3,4-epoxy-1-butene was 90.7% and selectivity to 2,5-dihydrofuran was 98.6%.

Extraction

The catalyst/oligomer residue remaining from the isomerization process was extracted with octane by the procedure described in Example 1. The catalyst-containing material (86.3 g) thus recovered had the following approximate composition: 22.3% triphenyltin iodide, 49.9% tetra-n-dodecylphosphonium iodide, and 27.9% oligomer. The amount of oligomer removed by the extraction procedure was 20.9 g.

EXAMPLE 8

Isomerization

The catalyst-containing material recovered in Example 7 was returned to the reaction flask and the isomerization procedure was repeated. Over a period of 21 hours, a total of 952 g of 3,4-epoxy-1-butene was added and 890 g of distillate was collected (93.5% weight recovery). The conversion of 3,4-epoxy-1-butene was 90.2% and selectivity to 2,5-dihydrofuran was 98.7%.

Extraction

The catalyst/oligomer residue remaining from the isomerization process was extracted with octane by the procedure described in Example 1. The catalyst-containing material (96.7 g) thus recovered had the following approximate composition: 16.5% triphenyltin iodide, 46.0% tetra-n-dodecylphosphonium iodide, and 37.5% oligomer. The amount of oligomer removed by the extraction procedure was 35.8 g.

Prior to using the catalyst-containing material in Example 9, 8.6 g triphenyltin iodide was added to it. The resulting material (105.3 g) contained 21.5% triphenyltin iodide, 44.5% tetra-n-dodecylphosphonium iodide, and 34.0% oligomer.

EXAMPLE 9

Isomerization

The catalyst-containing material recovered and supplemented with triphenyltin iodide in Example 8 was returned to the reaction flask and the isomerization procedure was repeated. Over a period of 16 hours, a total of 970 g of 3,4-epoxy-1-butene was added and 918 g of distillate was collected (94.6% weight recovery). The conversion of 3,4-epoxy 1-butene was 90.0% and selectivity to 2,5-dihydrofuran was 98.6%.

Extraction

The catalyst/oligomer residue remaining from the isomerization process was extracted with octane by the procedure described in Example 1. The catalyst-containing material (103.6 g) thus recovered had the following approximate composition: 19.9% triphenyltin iodide, 42.6% tetra-n-dodecylphosphonium iodide, and 37.5% oligomer. The amount of oligomer removed by the extraction procedure was 39.3 g.

The catalyst-containing material recovered in this example was recombined with the separated oligomer and the distribution coefficients for the triphenyltin iodide, tetra-n-dodecylphosphonium iodide, and oligomer were determined as described in Example 4 using octane and 80° C. The distribution coefficients and extraction selectivities determined are shown in Table I.

EXAMPLE 10

Isomerization

The procedure of Example 1 was repeated except that the initial charge of materials was tri-n-octyltin iodide (30.7 g), tri-n-octyl(n-octadecyl)phosphonium iodide (39.7 g), and 2,5-dihydrofuran (9.9 g). Over a period of 83 hours, a total of 2173 g of 3,4-epoxy-1-butene was added and 2082 g of distillate was collected (95.8% weight recovery). The conversion of 3,4-epoxy-1-butene was 91.5% and selectivity to 2,5-dihydrofuran was 99.1%.

Extraction

The catalyst/oligomer residue remaining from the isomerization process was extracted with octane using the procedure described in Example 1 to give 99.6 g of catalyst-containing material. The amount of oligomer removed by the extraction procedure was 14.8 g.

EXAMPLE 11

Isomerization

The catalyst-containing material recovered in Example 10 was returned to the reaction flask and the isomerization procedure was repeated. Over a period of 64 hours, a total of 1669 g of 3,4-epoxy-1-butene was added and 1596 g of distillate was collected (95.6% weight recovery). The conversion of 3,4-epoxy-1-butene was 90.6% and selectivity to 2,5-dihydrofuran was 98.9%.

Extraction

The catalyst/oligomer residue remaining from the isomerization process was extracted with octane by the procedure described in Example 1 to give 143.6 g of catalyst-containing material. The amount of oligomer removed by the extraction procedure was 36.4 g.

EXAMPLE 12

Isomerization

The catalyst-containing material recovered in Example 11 was returned to the reaction flask and the isomerization procedure was repeated. Over a period of 46 hours, a total of 1189 g of 3,4-epoxy-1-butene was added and 1141 g of distillate was collected (96.0% weight recovery). The conversion of 3,4-epoxy-1-butene was 88.9% and selectivity to 2,5-dihydrofuran was 98.7%.

Extraction

The catalyst/oligomer residue remaining from the isomerization process was extracted with octane by the procedure described in Example 1. The catalyst-containing material (97.4 g) thus recovered had the following approximate composition 34.9% tri-n-octyltin iodide, 41.3% tri-n-octyl(n-octadecyl)phosphonium iodide, and 23.8% oligomer. The amount of oligomer removed by the extraction procedure was 45.5 g.

The catalyst-containing material recovered in this example was recombined with the separated oligomer and the distribution coefficients for the tri-n-octyltin iodide, tri-n-octyl(n-octadecyl)phosphonium iodide, and oligomer were determined as described in Example 4 using octane and 60° C. The distribution coefficients and extraction selectivities determined are shown in Table I.

TABLE I

| Residue From Example | Average Distribution Coefficient | | | Average Extraction Selectivity | |
|---|---|---|---|---|---|
| | SNI | PHOS | OLIG | SNI | PHOS |
| 4A | 0.61 | 1.67 | 0.16 | 4.42 | 9.73 |
| 4B | 0.70 | 1.33 | 0.27 | 3.14 | 6.33 |
| 4C | 0.71 | 1.88 | 0.33 | 2.24 | 5.66 |
| 4D | 0.66 | 1.04 | 0.34 | 1.96 | 3.06 |
| 9 | 0.75 | 4.09 | 0.20 | 3.83 | 19.94 |

TABLE I-continued

| Residue From Example | Average Distribution Coefficient | | | Average Extraction Selectivity | |
|---|---|---|---|---|---|
| | SNI | PHOS | OLIG | SNI | PHOS |
| 12 | 0.85 | 0.91 | 0.18 | 4.39 | 4.65 |

The values reported in Table 1 establish the effectiveness of the extraction process provided by the present invention since the extraction selectivity only needs to be greater than unity for the extraction to be operable.

The invention has been described in detail with particular reference to preferred embodiments thereof, but it will be understood that variations and modifications can be effected within the spirit and scope of the invention.

We claim:

1. Process for the separation of a catalyst system comprising (i) an onium iodide compound, (ii) an organotin iodide compound, or (iii) a mixture thereof from a mixture of the catalyst system and an oligomer of a γ,δ-epoxyalkene by the steps comprising:
   (1) intimately contacting the mixture with an extraction solvent selected from hydrocarbons having about 5 to 12 carbon atoms and chlorocarbons;
   (2) allowing the mixture of step (1) to phase separate; and
   (3) recovering the extraction solvent phase containing iodide compounds (i) and/or (ii).

2. Process according to claim 1 wherein the γ,δ-epoxyalkene contains 4 to 8 carbon atoms and has the formula:

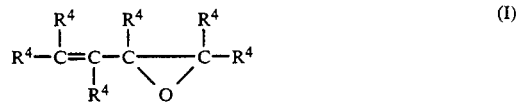

wherein each $R^4$ is independently selected from hydrogen and methyl or 2 $R^4$ substituents collectively may represent an alkylene radical which forms a ring having about 5 to 8 carbon atoms.

3. Process according to claim 1 wherein:
   the process is carried out at a temperature of about 40° to 125° C.
   the onium iodide compound is a tetra (hydrocarbyl)ammonium iodide or a tetra(hydrocarbyl)phosphonium iodides having a total carbon atom content of about 16 to 72 carbon atoms and formula:

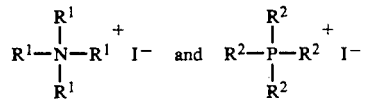

wherein
   each $R^1$ substituent independently is selected from alkyl of up to about 20 carbon atoms and each $R^2$ substituent is independently selected from $R^1$, benzyl, phenyl or phenyl substituted with up to 3 substituents selected from lower alkyl, lower alkoxy or halogen; or two $R^1$ substituents collectively may represent alkylene of 4 to 6 carbon atoms including alkylene of 4 to 6 carbon atoms substituted with lower alkyl;
   the organotin iodide compound has the formula:

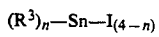

wherein each $R^3$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms; and n is 1, 2, or 3; and the γ,δ-epoxyalkene contains 4 to 8 carbon atoms and has the formula:

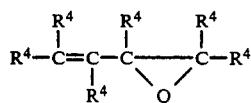

wherein each $R^4$ is independently selected from hydrogen and methyl.

4. Process according to claim 3 wherein the γ,δ-epoxy-alkene is 3,4-epoxy-1-butene.

5. Process for the separation of a catalyst system comprising (i) an onium iodide compound and (ii) an organotin iodide compound from a mixture of the catalyst system and an oligomer of 3,4-epoxy-1-butene by the steps comprising:

(1) intimately contacting the mixture with an extraction solvent selected from alkanes having about 6 to 12 carbon atoms;

(2) allowing the mixture of step (1) to phase separate; and (3) recovering the extraction solvent phase containing iodide compounds (i) and (ii);

wherein the onium compound is a phosphonium iodide containing about 32 to 72 carbon atoms and having the general formula:

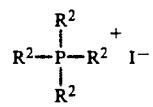

wherein each $R^2$ substituent is independently selected from straight-chain alkyl of about 4 to 18 carbon atoms; and the organotin iodide compound has the formula

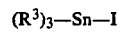

wherein each $R^3$ independently is selected from alkyl having about 4 to 10 carbon atoms or phenyl.

6. Process according to claim 6 wherein the process is carried out at a temperature of about 40° to 125° C. and the weight ratio of the extraction solvent to the catalyst/oligomer mixture is in the range of about 10:1 to 0.1:1.

7. Process for the separation of a catalyst system comprising (i) an onium iodide compound and (ii) an organotin iodide compound from a mixture of the catalyst system and an oligomer of 3,4-epoxy-1-butene by the steps comprising:

(1) intimately contacting the mixture with an extraction solvent selected from heptane, octane, nonane and decane at a temperature of about 40° to 125° C;

(2) allowing the mixture of step (1) to phase separate; and (3) recovering the extraction solvent phase containing iodide compounds (i) and (ii);

wherein the onium iodide compound is tetra-n-dodecylphosphonium iodide, tetra-n-hexadecylphosphonium iodide or tri-n-octyl(n-octadecyl)phosphonium iodide; and the organotin iodide compound is tri-n-octyltin iodide or triphenyltin iodide.

* * * * *

UNITED STATES PATENT AND TRADEMARK OFFICE
CERTIFICATE OF CORRECTION

PATENT NO. : 5,238,889

DATED : August 24, 1993

INVENTOR(S) : Falling et al.

It is certified that error appears in the above-identified patent and that said Letters Patent is hereby corrected as shown below:

On the title page, Item [75]:

After:
"N.Y.", ---; Timothy R. Nolen, Kingsport, Tenn.;
Jeffrey S. Kanel, Kingsport, Tenn. --- should be added.

Column 14, line 20 (Claim 6, line 1), "claim 6" should be --- claim 5 ---.

Signed and Sealed this

Eighth Day of March, 1994

Attest:

BRUCE LEHMAN

Attesting Officer     Commissioner of Patents and Trademarks